United States Patent [19]

Lin

[11] Patent Number: 4,906,798
[45] Date of Patent: Mar. 6, 1990

[54] HIGH VISCOSITY INDEX OLEFIN OLIGOMER PROCESS

[75] Inventor: Ronny W. Lin, Baton Rouge, La.

[73] Assignee: Ethyl Corporation, Richmond, Va.

[21] Appl. No.: 270,820

[22] Filed: Nov. 14, 1988

[51] Int. Cl.$^4$ ............................ C07C 2/02; C10L 1/16
[52] U.S. Cl. ........................................ 585/10; 585/12; 585/18; 585/255; 585/510; 585/532
[58] Field of Search ...................... 585/10, 12, 18, 255, 585/510, 532

[56] References Cited

U.S. PATENT DOCUMENTS

| | | | |
|---|---|---|---|
| 4,242,530 | 12/1980 | Smith | 585/510 |
| 4,282,392 | 8/1981 | Cupples et al. | 585/10 |
| 4,319,064 | 3/1982 | Heckelsberg et al. | 585/10 |
| 4,420,646 | 12/1983 | Darden et al. | 585/12 |
| 4,827,064 | 5/1989 | Wu | 585/10 |

Primary Examiner—Curtis R. Davis
Attorney, Agent, or Firm—J. D. Odenweller

[57] ABSTRACT

A high viscosity index olefin oligomer is made by feeding an olefin monomer near the top of a distillation column, maintaining the overhead temperature near the boiling point of the olefin monomer at system pressure and maintaining the bottom of the column and the reboiler at a temperature just above the boiling point of the highest boiling oligomer that is to be excluded from the product. An oligomerization catalyst (e.g. AlCl$_3$) is introduced into the column. The catalyst has a boiling point or sublimation temperature which is too low to permit passage out the bottom of the column and too high to cause it to escape out the top of the column.

19 Claims, 1 Drawing Sheet

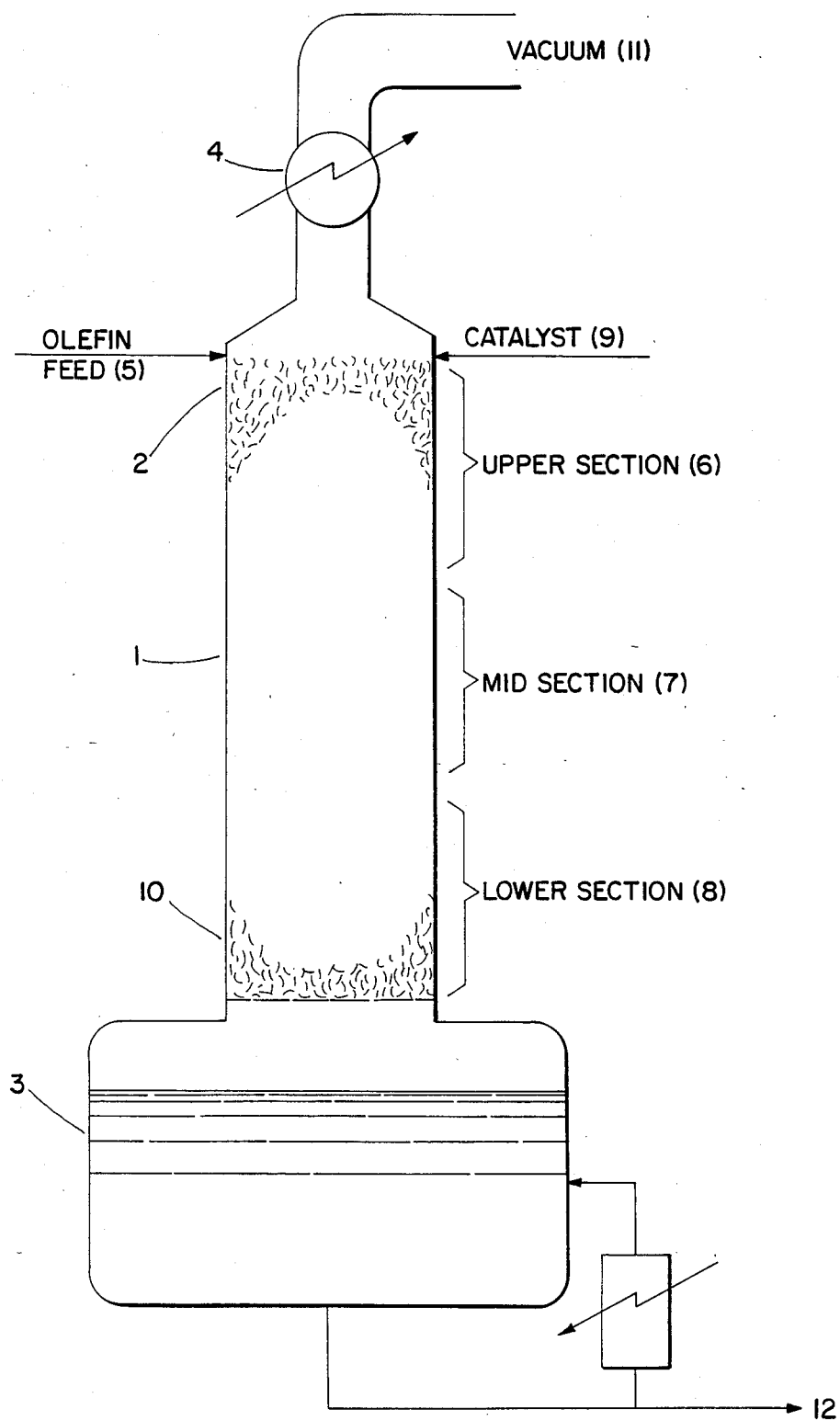

HIGH VISCOSITY INDEX OLEFIN OLIGOMER PROCESS

BACKGROUND

Alpha-olefin oligomers and their use as synthetic lubricants ("synlubes") are well-known. Early reports of such synlubes are in Seger et al. U.S. Pat. No. 2,500,161 and Garwood U.S. Pat. No. 2,500,163. U.S. Pat. No. 2,766,312 describes the oligomerization of α-olefins in a Group IV metal oxide bed using a $BF_3$ promoter catalyst. Promoters include water, alcohol and ether.

U.S. Pat. No. 3,149,178 describes the preparation of a synlube by oligomerizing a $C_{6-12}$ α-olefin thermally or using a Friedel Crafts or peroxide catalyst followed by distillation to remove dimer. The distillation residue is hydrogenated for use as a synlube. U.S. Pat. No. 3,382,291 discloses a $BF_3$-promoter (e.g. alcohol) process for making o-olefin oligomers in which the $BF_3$ is used to saturate the o-olefin feed and a second stream of $BF_3$-promoter is fed to the reaction.

Synlubes used as automotive crankcase lubricants have viscosities in the range of 4–8 cs at 100° C. These are usually mixture of trimers, tetramers and pentamers of $C_{8-12}$ α-olefins, especially 1-decene.

Recently extra high viscosity ("XHVI") mineral oil lubricants have been made available by new refining technology. Such XHVI oils have viscosity indices in the range of 145. These can be used as blending agents with lower viscosity mineral oil to obtain a blended oil suitable for use in an engine crankcase which approaches the performance of poly-alpha-olefin ("PAO") synlubes. It would be useful to be able to make an oil equivalent to XHVI mineral oil from olefin monomers.

SUMMARY

According to the present invention, a process is provided which makes available a novel high viscosity index olefin oligomer and is readily adaptable t continuous operation giving a substantially quantitative yield.

DESCRIPTION OF THE DRAWING

The drawing is a schematic representation of a distillation column including an upper section, a mid-section and a lower section used for carrying out the process of the invention.

DESCRIPTION OF THE PREFERRED EMBODIMENTS

A preferred embodiment is a process for making an olefin oligomer said process comprising:
(A) feeding a $C_{8-20}$ aliphatic monoolefin into a distillation column, said column having an upper section, a mid-section and a lower section,
(B) introducing an oligomerization catalyst into said column, said catalyst having a distillation or sublimation temperature below the temperature in said lower section such that a substantial amount of said catalyst remains in said column,
(C) maintaining said upper section at or just below the boiling point, at the pressure within said upper section, of said $C_{8-20}$ monoolefin feed,
(D) maintaining said column lower section at a temperature above the boiling point or sublimation temperature of said catalyst and above the boiling point, at the pressure within said column lower section, of oligomers to be excluded from the olefin oligomer product and
(E) removing the olefin oligomer product from said column lower section.

Monoolefins that can be used as feed stock for the process include any aliphatic monoolefin which contains in the range of about 8 to 20 carbon atoms. These can be vinyl or α-olefins, vinylidene olefins, internal olefins or mixtures of such olefins. The olefins can be straight or branched chain.

The preferred olefins contain at least 50 weight percent α-olefins. In a still more preferred embodiment the olefin feed stock is at least 75 weight percent α-olefins.

In a highly preferred embodiment the olefin feed stock is at least 50 weight straight chain olefins. In a more highly preferred embodiment the olefins are at least 75 weight percent straight chain olefins.

Although almost any aliphatic monoolefin can be used as a feed stock, the preferred olefins contain about 8–20 carbon atoms. In a more preferred embodiment the olefins contain about 8–16 carbon atoms. In a still more preferred embodiment, at least 80 weight percent of the olefins contain about 8–12 carbon atoms.

The most useful olefins are the aliphatic monoolefins containing about 8–12 carbon atoms and are at least 50 weight percent, more preferably at least 80 weight percent, α-olefins and at least 50 weight percent straight chain olefins. The most preferred feed stocks are 1-decene or $C_{8-12}$ olefin mixtures containing at least 75 weight percent 1-decene.

The catalysts used in the process must be capable of oligomerizing olefins and have a boiling point or sublimation temperature which is below the boiling point of the desired oligomer product. More preferably the catalyst will have a boiling point or sublimation temperature which is about equal to or above the boiling point of the olefin feed stock. Examples of such catalysts are $AlCl_3$ (subl. 178° C.), $FeCl_3$ (b.p. 280° C.), $GaCl_3$ (b.p. 215° C.) and $SnCl_4$ (b.p. 114.1° C.). The most preferred catalyst is $AlCl_3$.

PROCESS DESCRIPTION

The manner of carrying out the process is best explained by reference to the drawing. The reactor used to conduct the process is a distillation column 1. In the drawing the distillation column is a packing 2 type distillation column but other conventional distillation columns can be used such as a tray column. A packed column is preferred when $AlCl_3$ is used as the catalyst because a tray column might tend to plug. Distillation column 1 has an upper section 6, a mid-section 7 and a lower section 8. Distillation column 1 has a reboiler 3 at the bottom and a reflux condenser 4 at its top. The column 1, also includes a vacuum source 11, such as a steam jet, to lower the pressure within the column to the desired reduced pressure. The desired temperature is the highest temperature that can be tolerated by the product oligomer at bottom 10 of lower section 8 and in reboiler 3. The amount of vacuum required will vary with the starting olefin and the product made. For example, if the desired product is decene tetramer and higher oligomers, the pressure need not be reduced as low as would be required if the desired product was decene pentamer and higher oligomers. Likewise, if the desired product is decene hexamer and higher oligomer a still lower reduced pressure will be required to avoid thermal decomposition of product oligomer.

The optimum reduced pressure can be readily determined experimentally. A useful range in which to test is about 2 torr up to atmospheric. A preferred reduced pressure is about 2-100 torr, and still more preferably 2-20 torr.

In operation, monoolefin feed 5 is continuously introduced into upper section 6. Catalyst (AlCl$_3$ will be used in this description) is introduced into the column at 9. The catalyst can be dissolved in the monoolefin feed or fed separately to the column. The olefin feed starts to trickle down the column and encounters the AlCl$_3$ catalyst. The AlCl$_3$ catalyst concentrates in mid-section 7 because reboiler 3 and the bottom 10 of lower section 8 are maintained at a temperature which is above the sublimation temperature of AlCl$_3$ at the pressure within the reboiler and lower section. Midsection 7 and upper section 6 are maintained at a temperature at or below the sublimation temperature of AlCl$_3$ at column pressure. Under these conditions, olefin feed washes the AlCl$_3$ down to mid-section 7 where it is trapped because of the higher temperature in lower section 8 and reboiler 3.

As the olefin feed encounters the AlCl$_3$ catalyst, it oligomerizes forming dimers, trimers, tetramers and so forth which permits the oligomer to descend lower and lower in column 1. Reboiler 3 and bottom 10 of lower section 8 are maintained at a temperature high enough to prevent liquid from passing into reboiler 3 until it has been oligomerized to such a degree that its boiling point is at or above the temperature at bottom 10 of lower section 8 at the pressure within lower section 8. The oligomer product finally drains into reboiler 3. The liquid level in reboiler 3 is maintained at an operable level by removing product through conduit 12.

The following example serves to illustrate the process.

EXAMPLE

A distillation column (15.24 cm×2.22 cm dia.) packed with 0.6 cm glass rings was connected to a 500 ml distillation flask. A total reflux condenser and vacuum take-off was installed at the top of the column. Then 1.4 g of AlCl$_3$ was placed in the top of the column and vacuum was applied to lower column pressure to 5-10 torr. The wall temperature of the distillation flask (reboiler) was raised to 212° C. and continuous 1-decene feed to the top of the column was commenced. The overhead wall temperature was about 37° C. The decene trickled down the column together with AlCl$_3$ catalyst. After 10 minutes, liquid entered the reboiler at a liquid temperature of 222° C. After 1 hour 20 minutes, the oligomerization rate appeared to slow so the process was interrupted to add an additional 0.5 g of AlCl$_3$ to the column following which 1-decene feed was continued at 5-10 torr. After one hour 35 minutes lapsed time, the feed of 132 g of 1-decene was completed (reboiler temperature 214° C., overhead skin temperature 37° C.). The reboiler was held at 213°-222° C. at 5-10 torr for an additional 20 minutes and then cooled. A total of 118.3 g of oligomer was recovered from the reboiler. Its physical properties after water wash were:

Viscosity at 100° C.:18.23 cs
Viscosity at 40° C.: 142.7 cs
Viscosity Index:143
Pour Point: −51° C.

Molecular weight was determined by the gel permeation method which indicated the product was mainly heptamer and higher oligomers.

The unsaturated oligomers made by the process can be readily hydrogenated to obtain a saturated oligomer. Conventional hydrogenation catalysts such as a supported nickel catalyst can be used at hydrogenation temperature of about 150°-250° C. and hydrogen pressures of about 200-1000 psig.

The saturated oligomers made available by the new process represent another embodiment of the invention. These oligomers have viscosity indices which are equal or higher than the very-high (>125 VI) and extra-high (>145 VI) viscosity index lubricants described in U.S. Pat. No. 3,684,695; GB Nos. 1,342,499; 1,440,230; FR No. 2,109,237; GB No. 1,493,928 and Bull et al. "Proceedings of the 10th World Petroleum Congress". The present invention achieves this goal by providing a high viscosity index decene oligomer having a viscosity at 100° C. of at least 17 cs (centistokes), a viscosity at 40° C. of at least 125 cs, a viscosity index of at least 125 and consisting mainly of pentamer and higher oligomers as determined by gel permeation molecular weight.

The more preferred saturated decene oligomers made available by the new process exhibit a viscosity at 100° C. of 17-20 cs, a viscosity at 40° C. of 130-150 cs and have a viscosity index of at least 130, more preferably 140 or higher. These more preferred decene oligomers consist mainly of hexamer and higher decene oligomers as determined by gel permeation.

I claim:

1. A process for making an olefin oligomer said process comprising:
    (A) feeding a $C_{8-20}$ aliphatic monoolefin into a distillation column, said column having an upper section, a mid-section and a lower section,
    (B) introducing an oligomerization catalyst into said column, said catalyst having a distillation or sublimation temperature below the temperature in said lower section such that a substantial amount of said catalyst remains in said column,
    (C) maintaining said upper section at or just below the boiling point, at the pressure within said upper section, of said $C_{8-20}$ monoolefin feed,
    (D) maintaining said column lower section at a temperature above the boiling point or sublimation temperature of said catalyst and above the boiling point, at the pressure within said column lower section, of oligomers to be excluded from the olefin oligomer product and
    (E) removing the olefin oligomer product from said column lower section.

2. A process of claim 1 wherein said catalyst is AlCl$_3$.

3. A process of claim 2 wherein said monoolefin is at least 50 weight percent α-olefin.

4. A process of claim 3 wherein said monoolefins are at least 80 weight percent $C_{8-12}$ monoolefins.

5. A process of claim 4 wherein said monoolefins are at least 75 weight percent 1-decene.

6. A process of claim 1 conducted at reduced pressure such that the boiling point at such reduced pressure of the highest boiling undesired oligomer is below the temperature at which substantial decomposition of the olefin oligomers would occur.

7. A process of claim 6 wherein said catalyst is AlCl$_3$.

8. A process of claim 7 wherein said monoolefin feed is at least 50 weight percent α-olefin.

9. A process of claim 8 wherein said monoolefins are at least 80 weight percent $C_{8-12}$ monoolefins.

10. A process of claim 9 wherein said monoolefins are at least 75 weight percent 1-decene.

11. A process of claim 10 wherein the reduced pressure in said column lower section is in the range of 2-100 torr.

12. A process of claim 11 wherein the temperature in said column lower section is in the range of 100°-350° C.

13. A process for making a high viscosity index decene oligomer having a viscosity at 100° C. of 17-20 cs, a viscosity at 40° C of 130-150 cs and a viscosity index of at least 125, said process comprising:
(A) feeding 1-decene into a distillation column, said column having an upper section, a mid-section and a lower section,
(B) introducing a catalytic amount of AlCl$_3$ into said column,
(C) maintaining the top of said upper section at or just below the boiling point of 1decene at the pressure within said upper section whereby said 1-decene descends the column,
(D) maintaining the temperature at the bottom of said lower section above the boiling point of decene trimer and below the boiling point of decene tetramer at the pressure within said lower section,
(E) maintaining the pressure within said column in the range of about 2-20 torr and,
(F) removing said high viscosity index decene oligomer consisting essentially of tetramer and higher oligomers from said lower section.

14. A process of claim 13 wherein said temperature in said upper section is in the range of 20°-100° C. and said temperature in said lower section is in the range of 100°-300° C.

15. A process of claim 14 wherein said high viscosity index decene oligomer is removed from said lower section by draining into a column reboiler, said reboiler being maintained at a temperature at least as high as the temperature in said lower section.

16. A process of claim 13 wherein said temperature at the bottom of said lower section is maintained above the boiling point of decene trimer and below the boiling point of decene tetramer at the pressure within said lower section.

17. A process of claim 13 wherein said temperature at the bottom of said lower section is maintained above the boiling point of decene tetramer and below the boiling point of decene pentamer at the pressure within said lower section.

18. A high viscosity index saturated decene oligomer, said decene oligomer having a viscosity at 100° C. of at least 12 cs, a viscosity at 40° C. of at least 125 cs, a viscosity index of at least 125 and consisting mainly of pentamer and higher oligomers as determined by gel permeation molecular weight.

19. A high viscosity index decene saturated oligomer of claim 16 wherein said viscosity at 100° C. is 17-20 cs, said viscosity at 40° C. is 130-150 cs and said viscosity index is at least 130.

* * * * *